United States Patent
Aho et al.

(10) Patent No.: US 6,723,754 B2
(45) Date of Patent: Apr. 20, 2004

(54) USE OF COMT INHIBITORS AS ANALGESICS

(75) Inventors: Päivi Aho, Helsinki (FI); Inge-Britt Lindén, Espoo (FI)

(73) Assignee: Orion Corporation, Espoo (FI)

( * ) Notice: Subject to any disclaimer, the term of this patent is extended or adjusted under 35 U.S.C. 154(b) by 15 days.

(21) Appl. No.: 10/221,497

(22) PCT Filed: Mar. 16, 2001

(86) PCT No.: PCT/FI01/00265
§ 371 (c)(1),
(2), (4) Date: Sep. 13, 2002

(87) PCT Pub. No.: WO01/68083
PCT Pub. Date: Sep. 20, 2001

(65) Prior Publication Data
US 2003/0069316 A1 Apr. 10, 2003

(30) Foreign Application Priority Data
Mar. 17, 2000 (FI) .............................................. 20000635

(51) Int. Cl.$^7$ ............................................. A61K 31/045
(52) U.S. Cl. ........................................................ 514/728
(58) Field of Search ................................ 514/728, 727, 514/724

(56) References Cited

U.S. PATENT DOCUMENTS

| | | | |
|---|---|---|---|
| 5,112,861 A | | 5/1992 | Bäckstrom et al. |
| 5,236,952 A | * | 8/1993 | Bernauer et al. ............ 514/520 |
| 5,283,352 A | * | 2/1994 | Backstrom et al. ......... 558/401 |
| 5,389,653 A | | 2/1995 | Bernauer et al. |
| 5,446,194 A | | 8/1995 | Bäckstrom et al. |
| 5,470,737 A | * | 11/1995 | Weinshilboum et al. .... 435/371 |
| 5,489,614 A | | 2/1996 | Korkolainen et al. |
| 6,169,103 B1 | | 1/2001 | Purchase, Jr. et al. |
| 6,599,530 B2 | * | 7/2003 | Vahervuo .................... 424/464 |

FOREIGN PATENT DOCUMENTS

| | | |
|---|---|---|
| GB | 898879 | 6/1962 |
| WO | WO 96/37456 | 11/1996 |
| WO | WO 98/27973 | 7/1998 |

OTHER PUBLICATIONS

Walpole et al., "Analogues of Capsaicin with Agonist Activity as Novel Analgesic Agents; Structure–Activity Studies. 1. The Aromatic 'A–Region'," J. Med. Chem. vol. 36, pp. 2362–2372 (1993).
English abstract of Masatoshi et al., JP7215952 A 19950815, with attached first page of JP 7–215952.
Pertovaara et al., "Pain Behavior and Response Properties of Spinal Dorsal Horn Neurons Following Experimental Diabetic Neuropathy in the Rat: Modulation by Nitecapone, a COMT Inhibitor with Antioxidant Properties," Experimental Neurology, vol. 167, pp. 425–434 (2001).
S. H. Ferreira et al., "Bradykinin Initiates Cytokine–Mediated Inflammatory Hyperalgesia", Br. J. Pharmacol., vol. 110, pp. 1227–1231 (1993).
F. Q. Cunha et al., "Pharmacological Modulation Of Secondary Mediator Systems—Cyclic AMP And Cyclic GMP—On Inflammatory Hyperalgesia", British Journal of Pharmacology, vol. 127, pp. 671–678 (1999).
P. A. Aho et al., "Role Of Gastric Mucosal Eicosanoid Production In The Cytoprotection Induced By Nitecapone", Scand. J. Gastroenterol, vol. 27, pp. 134–138 (1992).
C. J. Sih et al., "Mechanism of Prostaglandin Biosynthesis", Journal of the American Chemical Society, vol. 92, p. 6670 (1970).
D. W. Busija et al., "Eicosanoid Synthesis Elicited By Norepinephrine In Piglet Parietal Cortex", Brain Research, vol. 403, pp. 243–248 (1987).
L. O. Randall et al., "A Method For Measurement Of Analgesic Activity On Inflamed Tissue", Arch. Int. Pharmacodyn., vol. 111, pp. 409–419 (1957).
K. Gyires et al., "The Use Of The Writhing Test In Mice For Screening Different Types Of Analgesics", Arch. Int. Pharmacodyn., vol. 267, pp. 131–140 (1984).
N. B. Eddy et al., "Synthetic Analgesics", J. Pharmacol. Ther., vol. 98, pp. 121–137 (1950).
E. Rivas et al., "In Vivo Effects Of New Inhibitors Of Catechol–O–Methyl Transferase". British Journal of Pharmacology, vol. 126, pp. 1667–1673 (1999).
R. A. Pérez et al., "Dihydroxynitrobenzaldehydes And Hydroxymethoxynitrobenzaldehydes: Synthesis And Biological Activity as Catechol–O–Methyltransferase Inhibitors", J. Med. Chem., vol. 35, pp. 4584–4588 (1992).
R. A. Pérez et al., "Inhibition Of Catechol–O–Methyltransferase By 1–Vinyl Derivatives Of Nitrocatechols And Nitroguaiacols", Biochemical Pharmacology, vol. 45, No. 10, pp. 1973–1981 (1993).
A. C. Eclöf et al., "Natriuretic And Vasodilating Effects of Dopamine Are Mimicked By Oral Administration of a Catechol–O–Methyltransferase (COMP) Inhibitor", J. Am. Soc. Nephrology, vol. 5, paragraph 23P, p. 657 (1994).
U. Holtbäck et al., "Regulators of Renal Dopamine Metabolism Control Salt Excretion", .J. Am. Soc. Nephrology, vol. 7, Paragraph A1922, p. 1633 (1996).
K. L. Green, "The Anti–Inflammatory Effect of Catecholamines In The Peritoneal Cavity And Hind Paw Of The Mouse", Br. J. Pharmac., vol. 45, pp. 322–332 (1972).
S. K. Bhattacharya et al., "Central Catecholaminergic Modulation Of Carrageenin–Induced Pedal Oedema in Rats", Res Exp Med, vol. 186, pp. 365–374 (1986).
M. Nakamura et al., "A Peripheral Sympathetic Component In Inflammatory Hyperalgesia", European Journal of Pharmacology, vol. 135, pp. 145–153 (1987).

* cited by examiner

*Primary Examiner*—Vickie Kim
(74) *Attorney, Agent, or Firm*—Finnegan, Henderson, Farabow, Garrett & Dunner, LLP

(57) ABSTRACT

The use of COMT inhibitors in the treatment of control of pain in mammals, for example in animals and humans.

6 Claims, No Drawings

USE OF COMT INHIBITORS AS ANALGESICS

This application is a national stage filing of PTC international Application No. PCT/FI01/00265, filed on Mar. 16, 2001. This application also claims the benefit of priority under 35 U.S.C. §119(a) to Finnish patent application no. 20000635, filed on Mar. 17, 2000.

FIELD OF THE INVENTION

The invention relates to the use of catechol-O-methyl transferase (COMT) inhibitors in the treatment or control of pain in mammals.

BRIEF DESCRIPTION OF THE PRIOR ART

Analgesic drugs can be divided into three groups: the nonopioid analgesics, the opioid analgesics and the adjuvant analgesics. The nonopioid analgesics such as aspirin, paracetamol and the nonsteroidal anti-inflammatory drugs (NSAIDs) like indomethacin and ibuprofen, act peripherally and in some cases also centrally through inhibition of various enzymes, mainly cyclooxygenase. The inhibition of cyclooxygenase leads to reduction in the hyperalgesic prostaglandins. The opioid analgesics produce analgesia through binding to the opiate receptors in the central nervous system. Adjuvant analgesics increase the analgesic effects of the opioids or act as analgesics themselves. This group of drugs include miscellaneous drugs e.g. anticonvulsants like carbamazepine, tricyclic antidepressants, steroids etc.

Inhibitors of catechol-O-methyl transferase (COMT) as well as methods for the preparation thereof are known in the prior art, e.g. in GB-A-2 200 109, EP-A-237 929 and WO-A-96 37456 as well as i.a. in British Journal of Pharmacology, vol.126, 1999, p.1667–1673 (E. Rivas et al.), in Journal of Medical Chemistry, vol.35(24), 1992, p.4584–4588 (R. A. Pérez et al.) and in Biochemical Pharmacology, vol.45(10), 1993, p.1973–1981 (R. A. Pérez et al.).

COMT is an enzyme which metabolises i.a. endogenous sympathomimetic catecholamines like dopamine and noradrenaline. COMT enzyme metabolises also exogenously adminstered catecholamines, e.g. levodopa. The inhibitors of COMT have been used i.a. in the treatment of Parkinson's disease for inhibiting the metabolism of levodopa. As specific examples i.a. entacapone ((E)-2-cyano-3-(3,4-dihydroxy-5-nitrophenyl)-N,N-diethyl-2-propenamide) and tolcapone (3,4-dihydroxy-4'-methyl-5-nitrobenzophenone) can be mentioned.

Furthermore, WO-A-98 27973 describes the use of the COMT inhibitors, especially nitecapone (3-(3,4-dihydroxy-5-nitrophenyl)methylene-2,4-pentanedione), in the prevention of diabetic vascular dysfunctions. Nitecapone is also known to have a natriuretic effect (Eklöf et al. J. Am. Soc. Nephrology 5 (3), 657, 1994, Holtbäck et al., J. Am. Soc. Nephrology, 7(9), 1633, 1996).

U.S. Pat. No. 5,489,614 discloses catechol derivatives useful as antioxidants in the prevention or treatment of tissue damage induced by lipid peroxidation.

SUMMARY OF THE INVENTION

The object of the invention is to provide further use of the COMT inhibitors, i.e. the use of COMT inhibitors in the treatment or control of pain in mammals, including animals and human beings.

DETAILED DESCRIPTION OF THE INVENTION

The applicant has found that inhibitors of COMT possess analgetic activity.

In the light of the prior art the role of the endogenous sympathomimetic catecholamines in inflammation and pain is controversial. Catecholamines have been reported to exhibit anti-inflammatory activity in certain animal models (K. L. Green, in Br. J. Pharmac., vol.45, 1972, p.322–332, and S. K. Bhattacharya and N. Das, in Res. Exp. Med., vol.186, 1986, p.365–374). However, they have also been shown to induce inflammatory hyperalgesia due to sensitization of the pain receptors (M. Nakamura and S. H. Ferreira, in Eur.J.Pharmacol., vol.135, 1987 p.145–153, S. H. Ferreira et al., in Br. J. Pharmacol. vol.110,1993, p.1227–1231, F. Q. Cunha et al., in Br. J. Pharmacol., vol.127, 1999, p.671–678). Therefore, it could be assumed that inhibition of the endogenous catecholamine metabolism caused by the COMT inhibitors would rather lead to increased inflammatory pain and not to analgesia as, however now found to be the case as shown below.

The analgesic action of the COMT-inhibitors is not considered to be due to the inhibition of the cyclooxygenase activity as is the case with the NSAIDs. On the contrary, one of the presently described compounds, nitecapone, has been shown to stimulate the formation of prostaglandins (P. A. Aho and I.-B. Linden. in Scand.J.Gastroenterol. vol.27, 1992, p.134–138). This is a common phenomenon for many catechol-structured compounds (C. J. Sih et al., in J. Am. Chem.Soc., vol.92(22), 1970, p.6670, and D. W. Busija and C. W. Leffler. in Brain Res., vol.403, 1987, p.243–248). Therefore, the mechanism of action for the analgesic activity of the COMT-inhibitors remains unclear.

Accordingly, the invention provides the use of COMT inhibitors for the treatment or control of pain of any origin, including acute and chronic pain.

A suitable structural subgroup of COMT inhibitors for use as analgesics are derivatives of a catechol compound. A further preferable subgroup of such catechol COMT inhibitors are those, wherein the catechol moiety bears an electronegative substituent at ortho-position to one of the hydroxy groups.

A further suitable catechol COMT inhibitors for the use of the invention are disclosed in the references cited above, e.g. in GB-A-2 200 109, EP-A-237 929 and WO-A-96 37456 and in the articles of R. A. Pérez et al. and E. Rivas et al, the contents of which are hereby incorporated by reference.

Thus a subgroup of catechol COMT-inhibitors suitable for use as analgesics are compounds of formula I as disclosed in GB-A-2 200 109, herein presented as compounds of formula Ia,

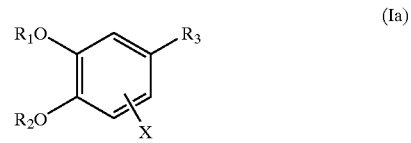

(Ia)

wherein $R_1$ and $R_2$ independently is H, alkyl, optionally substituted acyl or aryl, lower alkylsulfonyl or alkylcarbamoyl or taken together form a lower alkylidene or cycloalkylidene group, X comprises an electronegative substituent such as halogen, nitro, cyano, lower alkylsulfonyl, sulfonamido, aldehyde, carboxyl or trifluoromethyl; and $R_3$ is H, halogen, substituted alkyl, hydroxyalkyl, amino, nitro, cyano, trifluoromethyl, lower alkylsulfonyl, sulfonamido, aldehyde, alkyl carbonyl, aralkylidene carbonyl or carboxyl or a group selected from —CH=$CR_4R_5$ and —$CH_2$CH $R_4R_5$, wherein $R_4$ is H, alkyl, amino, cyano, carboxyl or acyl; and $R_5$ is H.

amino, cyano, carboxyl, alkoxycarbonyl, carboxy alkenyl, nitro, acyl, hydroxyalkyl, carboxyalkyl or an optionally substituted carboxamido, carbamoyl or aryl or heteroaroyl, or $R_4$ and $R_5$ together form a five to seven membered substituted cycloalkanone ring;

—$(CO)_n(CH_2)_m$—COR, wherein n is 0 or 1 and m is 0 or 1–7 and R is hydroxy, alkyl, carboxyalkyl, optionally substituted alkene, alkoxy or optionally substituted amino;

—$CONR_8R_9$, wherein $R_8$ and $R_9$ independently are H or one of the following optionally substituted groups; alkyl, alkenyl, alkynyl, cycloalkyl, aralkyl, or together form an optionally substituted piperidyl group; and —NH—CO—$R_{10}$, wherein $R_{10}$ is a substituted alkyl group, and the pharmaceutically acceptable salts thereof, as defined in GB-A-2 200 109. Preferably, $R_1$ and $R_2$ are H. Further preferably, X is at ortho-position to $R_2O$—.

A further subgroup of catechol COMT inhibitors suitable for use as analgesics are compounds of formula I as disclosed in WO-A-96 37456, herein presented as compounds of formula Ib,

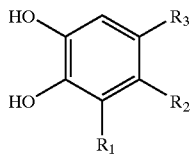

(Ib)

wherein $R_1$ is an electronegative substituent, preferably nitro, cyano, formyl or carboxy; $R_2$ is —A—$R_4$, wherein A is $(C_{1-9})$alkylene; $R_4$ is carboxy, 5-tetrazolyl, $R_5$ or CO—$R_5$; $R_5$ is phenyl or $(C_{3-7})$cycloalkyl which is substituted by at least one carboxy or 5-tetrazolyl; $R_3$ is an electronegative substituent, preferably nitro, cyano, halogen, formyl, carboxy, $(C_{1-5})$alkylcarbonyl, arylcarbonyl or $SO_2R_6$, wherein $R_6$ is $(C_{1-5})$alkyl, arylalkyl, aryl or $NR_7R_8$, wherein $R_7$ and $R_8$ are independently H, $(C_{1-5})$alkyl or together form a $(C_{3-6})$ ring, and the pharmaceutically acceptable esters or salts thereof, as defined in WO-A-96 37456.

Another subgroup of catechol COMT-inhibitors for use as analgesics are compounds of formula Ia as disclosed in EP-A-237 929, herein presented as compounds of formula Ic,

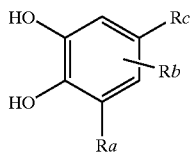

(Ic)

wherein Ra is nitro or cyano; Rb is H or halogen, Rc is halogen, nitro, cyano or a group —$(A)_n$—$(Q)_m$—$R^1$ or —$(A)_n$—Q—$R^2$, A is vinylene optionally substituted by lower alkyl, n is 0 or 1, m is 0 or 1, $R^1$ is —$COR^3$, an aromatic carbocyclic group or an aromatic or partially unsaturated heterocyclic group attached via a carbon atom, $R^2$ is H or an optionally substituted, saturated or partially unsaturated lower hydrocarbon residue, $R^3$ is hydroxy, amino, an optionally substituted, saturated or partially unsaturated lower hydrocarbon residue attached via an oxygen atom or an imino or lower alkylimino group or a saturated, N-containing heterocyclic group attached via a ring nitrogen atom, Q is the group —CO— or >C=N—$(Z)_p$—$R^4$, Z is an oxygen atom or an imino group, p is 0 or 1 and $R^4$ is H or a saturated or partially unsaturated, lower hydrocarbon residue which is optionally substituted and which is optionally attached via a carbonyl group, and physiologically hydrolyzable esters and ethers thereof as well as pharmaceutically acceptable salts thereof, as defined on EP-A-237 929.

Pharmaceutically acceptable salts and esters of these compounds, when applicable, may be prepared by known methods. The pharmaceutically acceptable salts are the usual organic and inorganic salts of the art. Such salts are well known in the literature.

The effective dose of the compound varies considerably depending on the efficacy of the COMT-inhibitor in question, the severity of the condition to be treated, and the route of administration. Most preferred are oral formulations. The effective dose for human beings is between 1 mg to 5000 mg per day, e.g. about 50–1000 mg per day.

The compounds according to this invention are given to a patient as such or in combination with one or more other active ingredients and/or suitable pharmaceutical excipients. The latter group comprises the conventionally used excipients and formulation aids, such as fillers, binders, disintegrating agents lubricants, solvents, gel forming agents, emulsifiers, stabilisers, colorants and/or preservatives.

The compounds used in this invention are formulated into dosage forms using commonly known pharmaceutical manufacturing methods. The dosage forms can be e.g. tablets, capsules, granules, suppositories, emulsions, suspensions or solutions. Depending on the route of administration and the galenic form, the concentration of the active compound in a formulation can typically vary between about 0.2 to 100% (w/w), e.g. 10 to 80% (w/w).

Choosing the suitable excipients for the formulation in question is routine for those of ordinary skill in the art.

Pharmacological Tests

There are several methods for testing analgesic drugs experimentally. The test of Randall Selitto (cf. e.g. L. O. Randall and J. J. Selitto, Arch.int.Pharmacodyn., vol.111(4), 1957, p.409–419) is based on the principal, that inflammation increases the sensitivity to pain. The inflammation is induced in the rat hind paw by yeast suspension and the pain threshold of the paw is measured. In the writhing test in mice an injection of dilute acetic acid elicit pain and so called writhing movements mainly through inflammation in the peritoneal area (K. Gyires and Z. Torma, in Arch.int.Pharmacodyn., vol.267, 1984, p.131–140). In these tests, both the NSAIDs and opioid analgesics are known to be effective. The hot plate test in mice is a test in which only opioid analgesics are effective.

The analgesic effect of the COMT inhibitors has been demonstrated below using compounds disclosed i.a. in the above-mentioned GB-A-2 200 109 and EP-A-237 929, i.e. nitecapone and entacapone (disclosed e.g. in GB-A-2 200 109, examples 7 and 100), as well as, 3',4'-dihydroxy-5'-nitroacetophenone and 3,5-dinitrocatechol (disclosed e.g. in EP-A-237 929, example 5 and the compound of formula Ia, wherein Ra and Rc are nitro and Rb is H), as the test compounds. The said COMT inhibitors were compared with a well known antiinflammatory analgetic, i.e. indomethacin.

Experiment I

The Test of Randall-Selitto

The effect on inflammatory pain was measured using a modified Randall-Selitto test. 0.1 ml of 20% Brewer's yeast suspension was injected subplantary to the right hind paw of rats under ether anaesthesia to elicit inflammation in the paw. After 3 hours the degree of hyperalgesia was determined with an analgesy-meter by applying a force of increasing magnitude to the inflamed paw with a cone-shaped teflon pusher. The force at which the animals begins to struggle was assumed to represent the pain threshold. The drugs were administered orally 5 ml/kg one hour before the measurement. The increase in pain threshold was calculated as a percentage of the control value.

Experiment II

Acetic Acid-induced Writhing in Mice

Acetic acid induced writhing test is a widely used screening method for analgesic agents. Both Anti-inflammatory analgesics (cyclo-oxygenase inhibitors) and narcotic analgesics are found to be effective in this model. Writing movements were elicited in mice by an i.p. injection of 1% acetic acid in the volume of 0.1 ml/10 g. The mice were placed in individual glass containers for observation. The number of writhes was counted during a period of 20 minutes and recorded every 5 minutes. The test compounds were given 5–60 minutes before the acetic acid.

The results of the EXPERIMENTS I and II are presented in table 1 and table 2.

TABLE 1

The effect of nitecapone, entacapone, 3',4'-dihydroxy-5'-nitroacetophenone and 3,5-dinitrocatechol on pain threshold of inflamed paw in rats (The Randall-Selitto test).

| Substance | Dose (mg/kg p.o.) | Increase in pain threshold (%) |
|---|---|---|
| Nitecapone | 0.5 | 13 |
|  | 1 | 58* |
|  | 3 | 46* |
|  | 10 | 45* |
| Entacapone | 10 | 62 |
|  | 30 | 64 |
| 3',4'-dihydroxy-5'-nitroacetophenone | 3 | 45 |
|  | 10 | 68** |
|  | 30 | 62* |
| 3,5-dinitrocatechol | 1 | 49* |
|  | 3 | 49* |
|  | 30 | 65* |
| Indomethacin | 1 | 54* |

*p < 0.05 vs. control group. n = 6–18

TABLE 2

The effect of nitecapone, entacapone, 3',4'-dihydroxy-5'-nitroacetophenone and 3,5-dinitrocatechol on acetic acid induced writhing in mice.

| Substance | Dose (mg/kg) | Route of administration | Inhibition of writhing (%) |
|---|---|---|---|
| Nitecapone | 50 | p.o | 15* |
|  | 100 | p.o. | 21** |
|  | 30 | i.p. | 37* |
|  | 100 | i.p. | 76* |
| Entacapone | 100 | p.o. | 24 |
|  | 3 | i.v. | 14 |
|  | 10 | i.v. | 38* |

TABLE 2-continued

The effect of nitecapone, entacapone, 3',4'-dihydroxy-5'-nitroacetophenone and 3,5-dinitrocatechol on acetic acid induced writhing in mice.

| Substance | Dose (mg/kg) | Route of administration | Inhibition of writhing (%) |
|---|---|---|---|
| 3',4'-dihydroxy-5'-nitroacetophenone | 50 | p.o. | 28** |
|  | 100 | p.o. | 43** |
| 3,5-dinitrocatechol | 50 | p.o. | 36** |
|  | 100 | p.o. | 22** |
| Indomethacin | 2 | p.o. | 18* |
|  | 6 | p.o. | 42** |
|  | 1 | i.p. | 38* |

*p < 0.05,
**p < 0.01 vs. control group. n = 6–12

The data show that the tested COMT-inhibitors were able to significantly decrease the pain threshold in the inflamed paw in the test of Randall-Selitto (cf. table 1). The tested compounds were also shown to be analgesic in the acetic acid induced writhing test in mice (cf. table 2).

Experiment III

The Hot Plate Test in Mice

Hot plate is used to evaluate whether a compound has centrally mediated analgesic. The method was modified from Eddy et al. using a thermostatically controlled metal plate activity (N. B. Eddy et al.: Synthetic analgesics, J Pharmacol Ther 98:121, 1950). The time interval between dropping a mouse to the hot plate (55.5° C.) and its reaction to the heat was measured. Licking of hind paws or jumping was considered as the end point. Each mouse was kept on the hot plate for a maximum of 60 seconds. A control reaction time for each animal was measured. 30 minutes later the test compounds were administered orally. The reaction time was measured again 0.5, 1 and 2 hours after the drug administration.

The COMT-inhibitors tested had no effect in the hot plate test, in which narcotic analgesic agents are found to be effective. The results indicate, that the analgesic effect of the COMT inhibitors is not mediated through central nervous system, namely through opioid receptors, but through some peripheral mechanism.

What is claimed is:

1. A method for the treatment of pain, said method comprising administering to a mammal in need of treating pain an effective amount of a COMT inhibitor or a pharmaceutically acceptable salt or ester thereof wherein the COMT inhibitor is a derivative of a catechol compound.

2. The method according to claim 1, wherein the derivative of a catechol compound has an electronegative substituent at an ortho-position to one of the hydroxy groups of the catechol moiety.

3. The method according to claim 1, wherein said COMT inhibitor is selected from nitecapone, entacapone and tolcapone.

4. The method according to claim 1, wherein said COMT inhibitor is nitecapone.

5. The method according to claim 1, wherein the pain is acute pain.

6. The method according to claim 1, wherein the pain is chronic pain.

* * * * *